United States Patent
Yu et al.

(10) Patent No.: US 11,223,755 B2
(45) Date of Patent: *Jan. 11, 2022

(54) IMAGE SCANNING, DISPLAYING AND LIGHTING SYSTEM FOR ELIMINATING COLOR DIFFERENCE

(71) Applicants: CENTRAL WISDOM TECHNOLOGY CONSULTING CORP., Taoyuan (TW); JIA CHEN GLOBAL DENTAL INSTRUMENT CO., LTD., Taipei (TW)

(72) Inventors: Yeh-Wei Yu, Taoyuan (TW); Ching-Cherng Sun, Taoyuan (TW); Tsung-Hsun Yang, Taoyuan (TW); Jia-Min Chuang, Taipei (TW)

(73) Assignee: eSHADE TECHNOLOGY CO., LTD., Taipei (TW)

( * ) Notice: Subject to any disclaimer, the term of this patent is extended or adjusted under 35 U.S.C. 154(b) by 0 days.

This patent is subject to a terminal disclaimer.

(21) Appl. No.: 16/729,283

(22) Filed: Dec. 27, 2019

(65) Prior Publication Data

US 2021/0105446 A1   Apr. 8, 2021

(30) Foreign Application Priority Data

Oct. 8, 2019 (TW) ................. 108136328

(51) Int. Cl.
*H04N 5/225* (2006.01)
*H04N 9/04* (2006.01)
(Continued)

(52) U.S. Cl.
CPC ......... *H04N 5/2256* (2013.01); *H04N 9/0455* (2018.08); *H04N 9/04521* (2018.08);
(Continued)

(58) Field of Classification Search
None
See application file for complete search history.

(56) References Cited

U.S. PATENT DOCUMENTS

2006/0082679 A1* 4/2006 Chua ................... H04N 5/2354 348/371
2008/0137324 A1* 6/2008 Pastore ................. G03B 15/06 362/16

(Continued)

*Primary Examiner* — Twyler L Haskins
*Assistant Examiner* — Wesley J Chiu
(74) *Attorney, Agent, or Firm* — Juan Carlos A. Marquez; Marquez IP Law Office, PLLC

(57) ABSTRACT

An image scanning, displaying and lighting system for eliminating color differences is revealed. The system includes an image scanner, a display screen with a second emission spectrum and a lighting device with a third emission spectrum. The image scanner consists of an optoelectronic image capturing and forming system, a plurality of first light sources disposed around the optoelectronic image capturing and forming system and a control module. The first light sources have a first emission spectrum which is a white light composed of a plurality of wavebands with different peak wavelengths. The control module controls the optoelectronic image capturing and forming system to take monochrome images in different colors in time sequence. The second emission spectrum has the same characteristics as the first emission spectrum while the third emission spectrum has the same characteristics as the second emission spectrum.

11 Claims, 7 Drawing Sheets

(51) Int. Cl.
   *H04N 9/64*   (2006.01)
   *H04N 9/07*   (2006.01)
   *A61C 9/00*   (2006.01)
   *A61B 1/24*   (2006.01)

(52) U.S. Cl.
   CPC .............. *H04N 9/07* (2013.01); *H04N 9/646* (2013.01); *A61B 1/24* (2013.01); *A61C 9/0053* (2013.01)

(56) References Cited

U.S. PATENT DOCUMENTS

| | | | |
|---|---|---|---|
| 2012/0044374 A1* | 2/2012 | Pohlert | H04N 5/2256 348/220.1 |
| 2012/0121245 A1* | 5/2012 | Messina | G02B 19/0028 396/199 |
| 2013/0256638 A1* | 10/2013 | Uesugi | H01L 27/3276 257/40 |
| 2014/0313366 A1* | 10/2014 | Lee | H04N 5/265 348/222.1 |
| 2014/0333759 A1* | 11/2014 | White | H04N 5/225 348/125 |
| 2016/0018575 A1* | 1/2016 | Chen | H01L 27/322 359/887 |
| 2016/0065826 A1* | 3/2016 | Chan | H04N 5/23203 348/211.2 |
| 2016/0094763 A1* | 3/2016 | Patel | H04N 5/23241 348/333.13 |
| 2017/0170200 A1* | 6/2017 | Ikeda | G09G 3/2003 |
| 2018/0226016 A1* | 8/2018 | Suzuki | G09F 9/30 |
| 2018/0367786 A1* | 12/2018 | Furst | G01J 3/027 |
| 2020/0111193 A1* | 4/2020 | Rephaeli | H04N 9/04521 |
| 2020/0252598 A1* | 8/2020 | Ida | H04N 13/254 |
| 2020/0295310 A1* | 9/2020 | Moon | H01L 51/5253 |
| 2020/0404189 A1* | 12/2020 | Talbert | H04N 5/2621 |
| 2021/0074775 A1* | 3/2021 | Gallagher | H01L 51/5271 |

* cited by examiner

IMAGE SCANNING, DISPLAYING AND LIGHTING SYSTEM FOR ELIMINATING COLOR DIFFERENCE

BACKGROUND OF THE INVENTION

1. Technical Field

The present invention relates to an image scanning, displaying and lighting system for eliminating color differences, especially to an scanning, displaying and lighting system for eliminating color differences occurred during image scanning by electronic devices, image display by display screens and lighting provided for replicating teeth or other objects.

2. Description of Related Art

The era of information has arrived. The traditional manual operations are replaced by applications of information technology. For example, each step during the creation of denture models and the following production processes needs professional techniques of dentists and dental technicians. As to sampling and color comparison in clothing industry, these also take labors and some expert's experience. Moreover, the shoes can be designed in America, sampled in Asia and then sent back to American for confirmation. All these manual operations and sample confirmation processes have limits in distance, time and efficiency.

Take denture fabrication as an example. First dentists take measurements for getting denture models and impressions and perform color-matching of dental plates/or use dental shade guide for color-matching manually to ensure the best match for the needs. Next both the dental model and relevant information such as the dental shade guide or dental plates for color-matching are shipped to dental laboratories. Then the dental model is carved and painted with colors required by dental technicians and shipped back to the dental clinic. During these processes, not only the denture model is shipped long-distance or cross-country, making dentures also requires intense labor work for each step including creating dental models, color matching, carving and painting. Thereby the denture fabrication is difficult to move to mass production.

In the conventional way, the images of teeth in the oral cavity are taken by the camera and then are shown on the display screen for matching colors or shades. Once the spectrum of the light sources in image-capturing environments and the spectrum of the display screen are not consistent, this would cause severe color differences. In order to avoid problems caused by shipping of the dental model or the denture, the dental model images are transmitted to the dental laboratory and show on the display screen for replacement of the dental model. Then the dental technicians carve the mold and apply colors to the dentures. At the moment, the color difference problem also occurs if the spectrum of ambient light for the workbench is not consistent with the spectrum of the display screen used for showing the dental mold images.

During denture fabrication, not only the 3D shape of the denture which has a certain effect on occlusion but also perfect color-matching with existing teeth should be considered for aesthetic purposes. In the conventional, the electronic devices are used to take images and the display screens are used to show the images taken. An auxiliary light source is also disposed beside the workbench for providing light during denture processing. A little color difference among different devices used during denture fabrication results in severe color distortion in each step of the fabrication process. These are the biggest challenges in long-distance production, cross-country production, informatization, automated production and intelligent production of the dentures. Thus there is a room for improvement and there is a need to provide a novel system for solving the problems mentioned above.

SUMMARY OF THE INVENTION

Therefore it is a primary object of the present invention to provide an image scanning, displaying and lighting system which is mainly used to solve the color difference problem of the same object among different electronic devices occurred during image scanning, displaying and/or lighting for image capturing, image formation, and image comparison made during object replication.

The present invention provides an image scanning, displaying and lighting system for eliminating color differences comprising: an image scanner which includes an optoelectronic image capturing and forming system, a plurality of first light sources disposed around the optoelectronic image capturing and forming system and having a first emission spectrum, and a control module for control of the optoelectronic image capturing and forming system to take monochrome images in different colors in time sequence; a display screen having a second emission spectrum with the same characteristics as the first emission spectrum; and a lighting device having a third emission spectrum with the same characteristics as the second emission spectrum. The first emission spectrum is a white light composed of a plurality of wavebands with different peak wavelengths in wavelength regions of a plurality of colors.

The present invention provides a displaying and lighting system for eliminating color differences comprising: a display screen having a second emission spectrum with the same characteristics as the first emission spectrum; and a lighting device having a third emission spectrum with the same characteristics as the second emission spectrum.

Implementation of the present invention at least produces the following advantageous effects:
1. The color variations between the image scanner and the display screen can be eliminated.
2. The color difference problem between the display screen and the lighting device can be solved.
3. The color differences among the image scanner, the display screen and the lighting device can be avoided.
4. The problems related to timeliness and cost of dental molds/or samples caused by long-distance delivery can be solved.
5. Based on the above solutions, cross-border production and intelligent fabrication flow of the denture industry can be achieved.

BRIEF DESCRIPTION OF THE DRAWINGS

The structure and the technical means adopted by the present invention to achieve the above and other objects can be best understood by referring to the following detailed description of the preferred embodiments and the accompanying drawings, wherein.

DETAILED DESCRIPTION OF THE INVENTION

Figure 1:
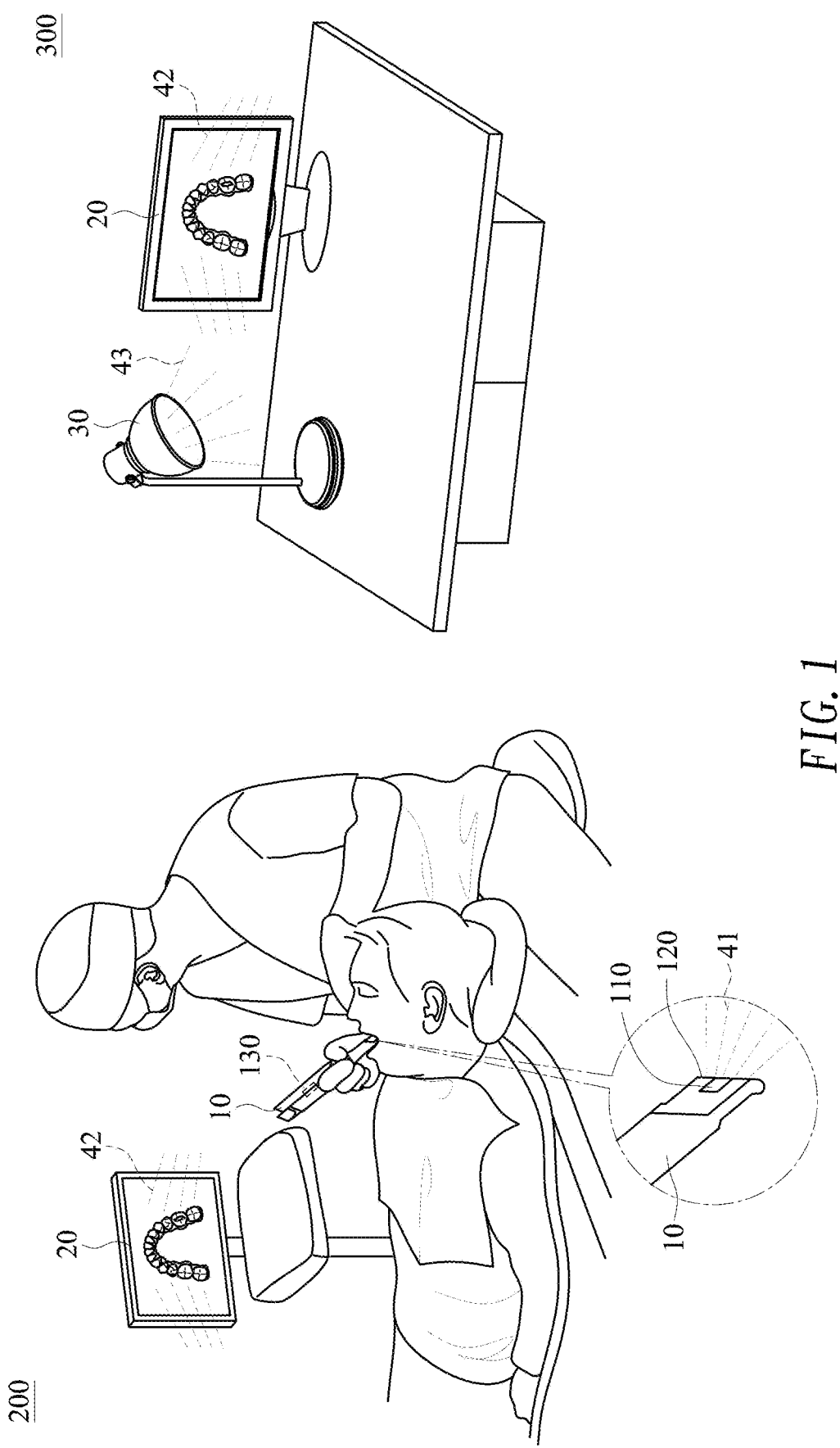
FIG. 1 is a schematic drawing showing environments in the dental clinic and the dental laboratory according to the present invention.
Figure 2:
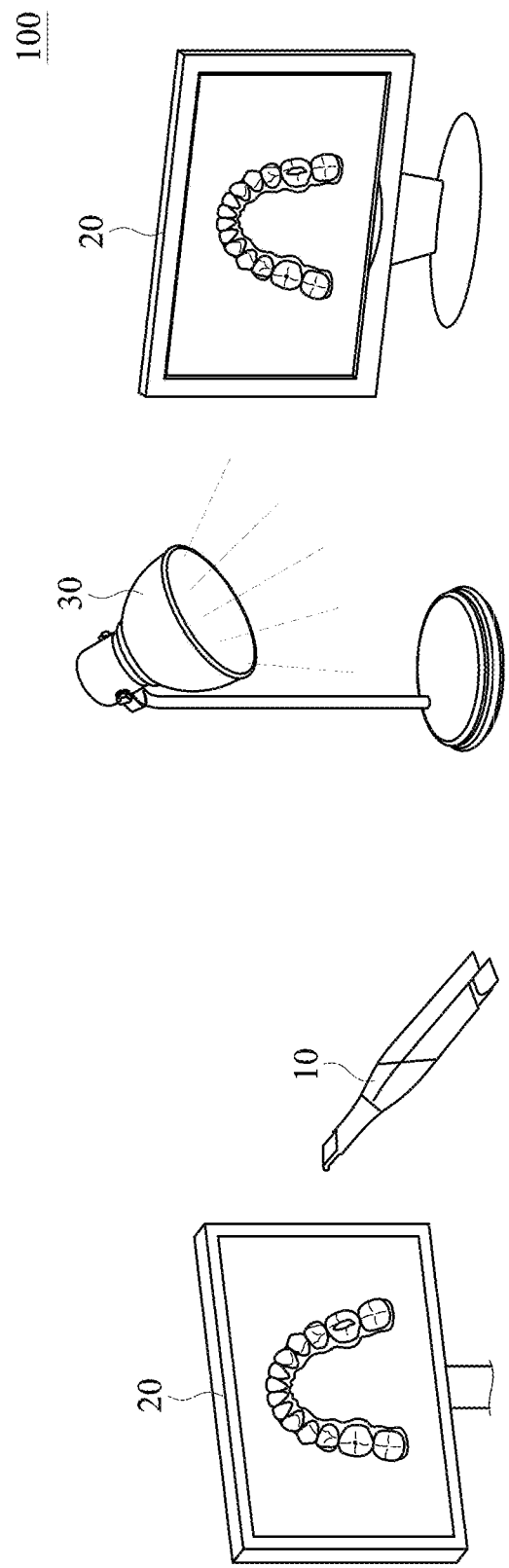
FIG. 2 is a schematic drawing showing an image scanning, displaying and lighting system for eliminating color differences y an embodiment according to the present invention.

As shown in FIG. 1 and FIG. 2, an image scanning, displaying and lighting system for eliminating color differences 100 according to the present invention includes an image scanner 10, a display screen 20 and a lighting device 30.

While in use, the image scanner 10 at one end capture images of samples for sampling and color-picking. Then the images are shown on the display screen 20 at the site where they are taken for checking the colors and the shapes. Or the images of the samples are sent to the processing site at the remote end and shown on the display screen 20 therein for being used as templates for creating products. A workbench is provided with the lighting device 30. There is no color variance among the image scanner 10, the display screen 20, and the lighting device 30 involved in the workflow. That means the same spectrum is used in the image scanner 10, the display screen 20 and the lighting device 30 to avoid color differences between the templates and the products. Thus the product produced looks identical to the sample.

The present invention can be particularly applied to various fields such as denture manufacturing processes, textile manufacturing processes, shoe manufacturing processes, etc. to avoid color mismatch between the original sample and the product caused by color differences among devices (such as sampling equipment, display screens) and lighting device in production environments or environment differences.

Take the denture manufacturing process as an example. The present system mainly provides the following effects. 1. The color variations between the image scanner 10 and the display screen 20 in the dental clinic/hospital 200 can be eliminated. 2. The color difference problem between the display screen 20 and the lighting device 30 disposed in the dental laboratory 300 can be solved. 3. The color differences among all devices involved including the image scanner 10, the display screen 20 and the lighting device 30 arranged at the dental clinic/hospital 200 and the dental laboratory 300 can be eliminated. By all of the above devices having the same standard spectrum, the color mismatch problem caused by color differences among the devices used in the denture fabrication process can be avoided.

Figure 3A:
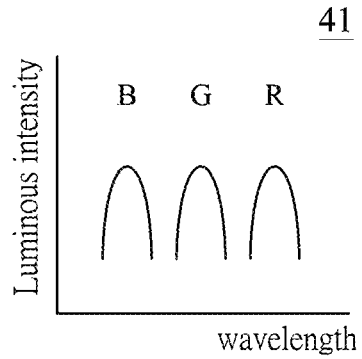
FIG. 3A shows a first emission spectrum having peaks in the regions of three colors, a second emission spectrum having peaks in the regions of three colors, and a third emission spectrum having peaks in the regions of three colors of an embodiment according to the present invention.
Figure 3A:
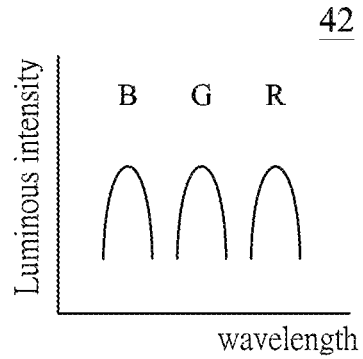
Figure 3A:
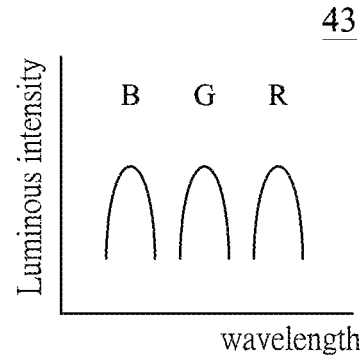
Figure 3B:
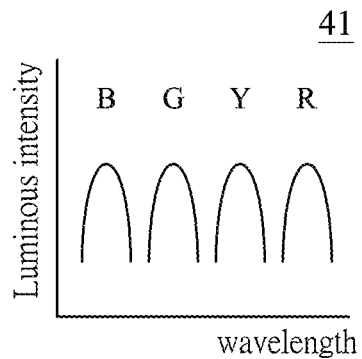
FIG. 3B shows a first emission spectrum having peaks in the regions of four colors, a second emission spectrum having peaks in the regions of four colors, and a third emission spectrum having peaks in the regions of four colors of an embodiment according to the present invention.
Figure 3B:
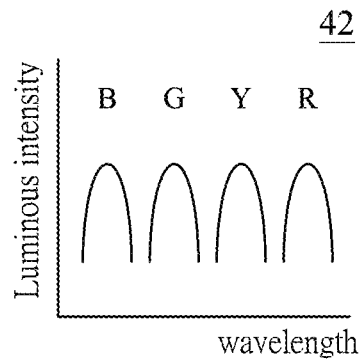
Figure 3B:
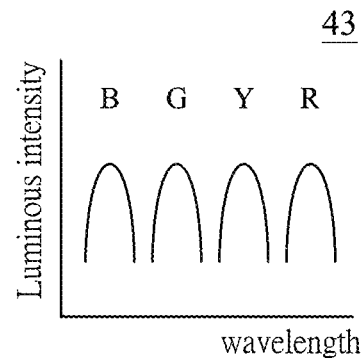
Figure 3C:
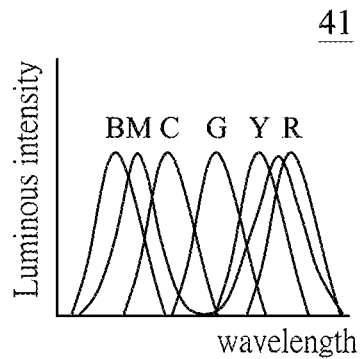
FIG. 3C shows a first emission spectrum having peaks in the regions of six colors, a second emission spectrum having peaks in the regions of six colors, and a third emission spectrum having peaks in the regions of six colors of an embodiment according to the present invention.
Figure 3C:
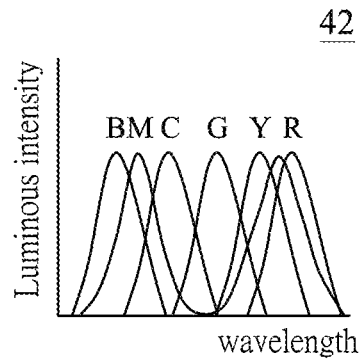
Figure 3C:
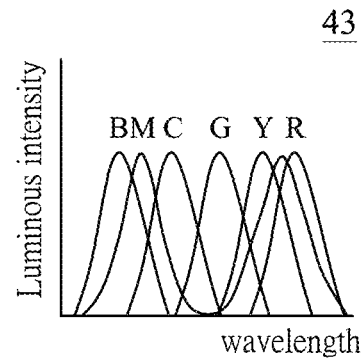

Refer to FIG. 3A and FIG. 3C, the technical features of the present system is in that the image scanner 10, the display screen 20 and the lighting device 30 are respectively having a first emission spectrum 41, a second emission spectrum 42, and a third emission spectrum 43. The first emission spectrum 41, the second emission spectrum 42, and the third emission spectrum 43 are all white light composed of a plurality of wavebands with different peak wavelengths, having the same characteristics or the same characteristic curves. Thereby the first emission spectrum 41, the second emission spectrum 42, and the third emission spectrum 43 have a common standard spectrum to solve the problem of color differences resulted from the equipment itself.

The peak wavelengths of the wavebands of the first emission spectrum 41, the second emission spectrum 42, and the third emission spectrum 43 are in the red, green and blue regions. Each of the first emission spectrum 41, the second emission spectrum 42, and the third emission spectrum 43 is a three-color spectrum formed by a combination of the same red (R), green (G), and blue (B) colors.

Moreover, the peak wavelengths of the wavebands of the first emission spectrum 41, the second emission spectrum 42, and the third emission spectrum 43 are in the red, green, blue and yellow regions. Each of the first emission spectrum, the second emission spectrum, and the third emission spectrum is a four-color spectrum composed of the same red (R), green (G), blue (B), and yellow (Y) colors.

The peak wavelengths of the wavebands of the first emission spectrum 41, the second emission spectrum 42, and the third emission spectrum 43 are in the red, green, blue, cyan, magenta and yellow regions. Each of the first emission spectrum, the second emission spectrum, and the third emission spectrum is a six-color spectrum represented as a combination of the same red (R), green (G), blue (B), cyan (C), magenta (M) and yellow (Y) colors.

Figure 4A:
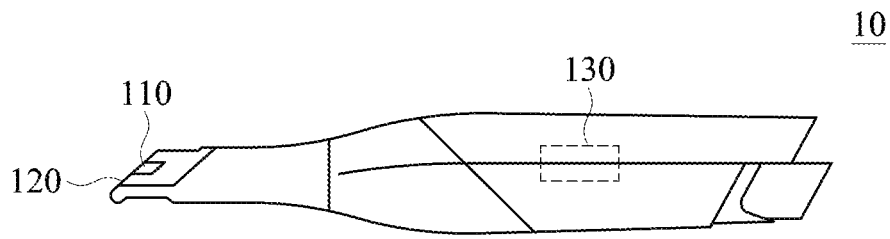
FIG. 4A is a perspective view of an image scanner of an embodiment according to the present invention.
Figure 4B:
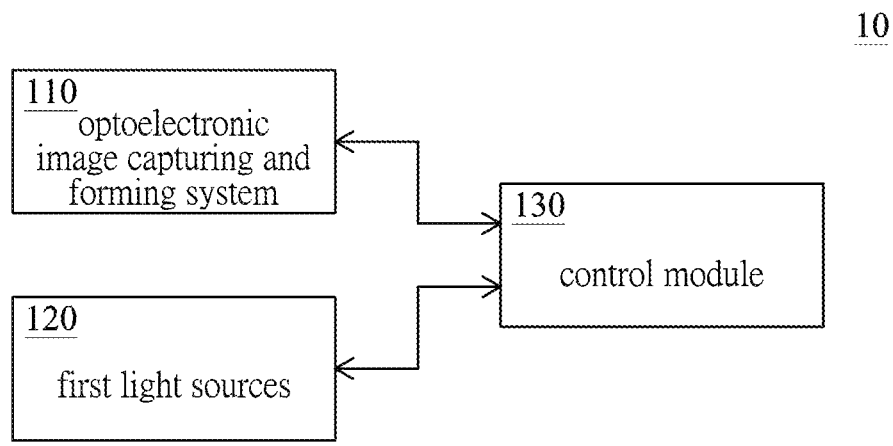
FIG. 4B is a circuit block diagram of an image scanner of an embodiment according to the present invention.

As shown in FIG. 4A and FIG. 4B, the image scanner 10 which consists of an optoelectronic image capturing and forming system 110, a plurality of first light sources 120 and a control module 130 is a handheld device. During fabrication of dentures used for treatment related to oral cavity, the image scanner 10 is used to scan patient's teeth in the oral cavity for 2D or 3D sampling so as to achieve the best color match to the patient's existing teeth.

The optoelectronic image capturing and forming system 110 mainly includes a complementary metal oxide semiconductor (CMOS) component or a charge-coupled device (CCD) used as the photoelectric conversion device. After capturing images of the teeth in the oral cavity by the optoelectronic image capturing and forming system 110, the above photoelectric conversion device converts optical signals into electrical signals so that the following transmission and image processing can be performed conveniently. The optoelectronic image capturing and forming system 110 further includes an imaging optical system in order to form images.

Figure 5:
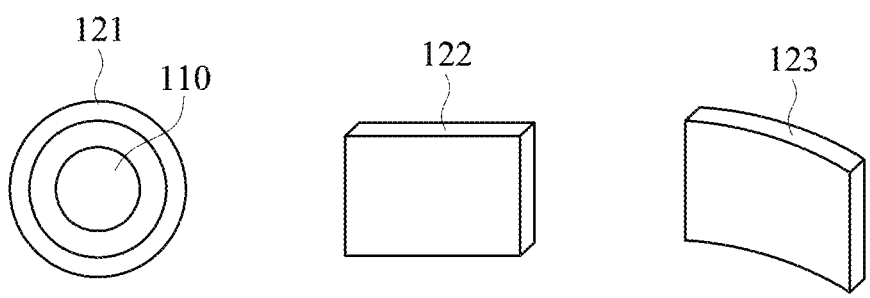
FIG. 5 shows embodiments of a first light source according to the present invention.
Figure 6A:
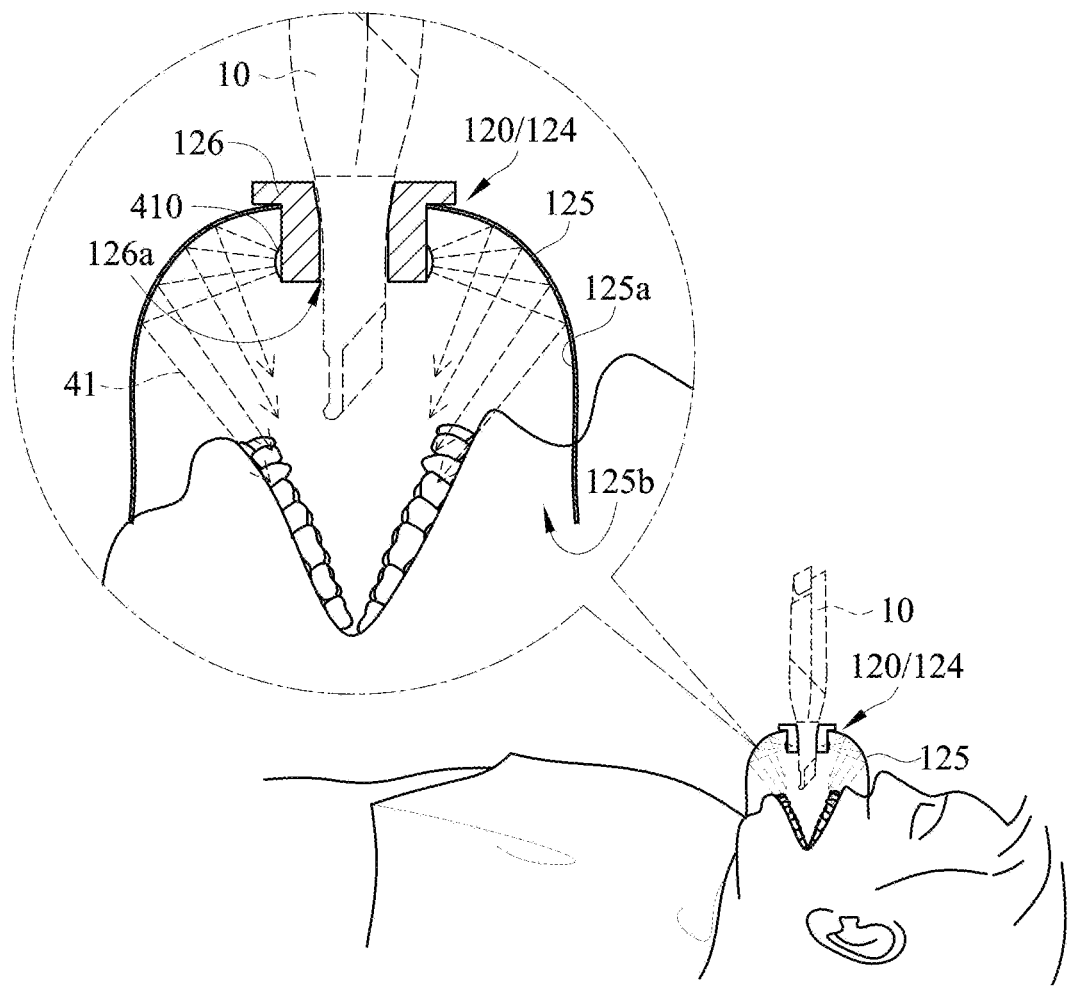
FIG. 6A is a schematic drawing showing a masked light source of an embodiment in use according to the present invention.
Figure 6B:
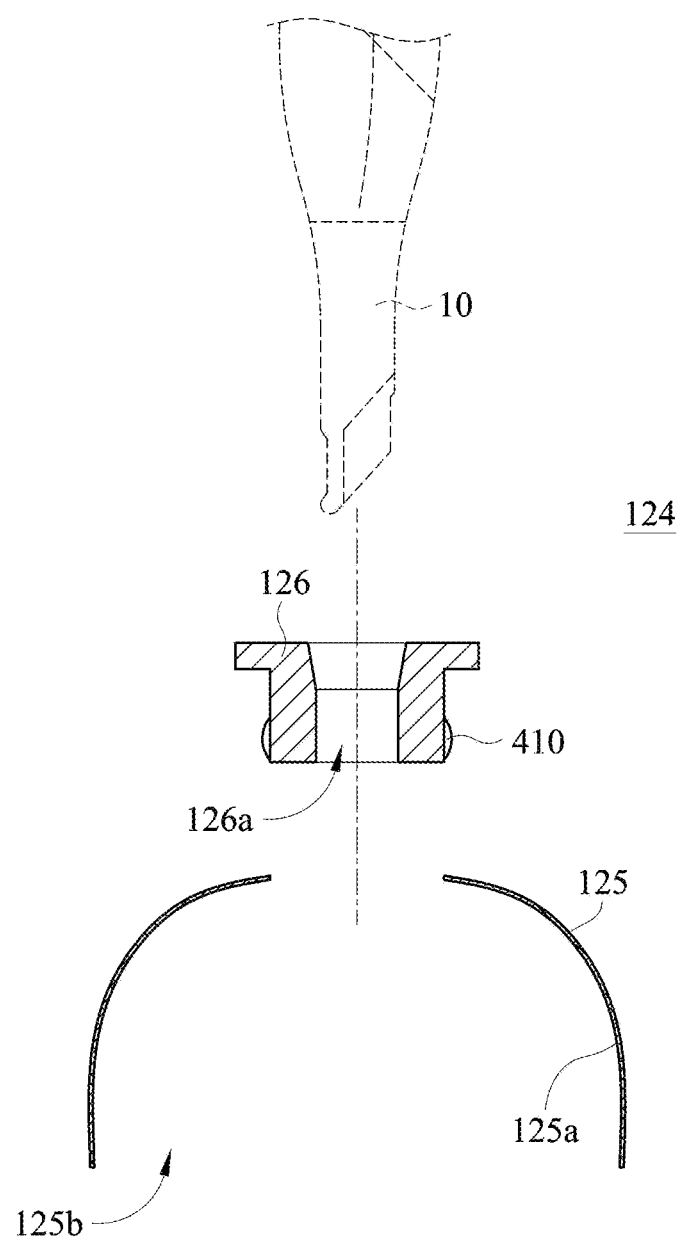
FIG. 6B is an explosive view of a masked light source of an embodiment according to the present invention.

Refer to FIG. 5, FIG. 6A and FIG. 6B, the first light source 120 can be designed into a ring light source 121, a planar light source 122 or a curved surface light source 123. Besides, it can also be designed into a masked light source 124 composed of a mask 125 and a plastic part 126.

The mask 125 that looks like an oxygen mask is an opaque circular wall with a reflecting surface 125*a* therein. A mask opening 125*b* is formed on a skirt portion of the mask 125 and used for shading and covering the patient's oral cavity.

The plastic part 126 is a hollow cylinder formed on top of the mask 125, extending toward the inner space of the mask 125 and provided with a connection through-hole 126*a*. The first light sources 120 can be arranged at an outer surface of the plastic part 126 to project the first emission spectrum onto the reflecting surface 125*a* of the mask 125.

The connection through-hole 126*a* is for allowing the optoelectronic image capturing and forming system 110 to insert therein. After being projected onto the reflecting surface 125*a* in the mask 125, the first emission spectrum from the first light sources 120 is reflected again and projected onto the patient's teeth. Thereby the optoelectronic image capturing and forming system 110 can capture images under light with the first emission spectrum.

The first light sources 120 are designed to have the first emission spectrum 41 which is a white light composed of a plurality of wavebands with different peak wavelengths. The first light sources 120 are disposed around the optoelectronic image capturing and forming system 110 for filling light so that not only the image scanner 10 can get clear images, standard images can also be created using the standard spectrum.

Figure 7A:
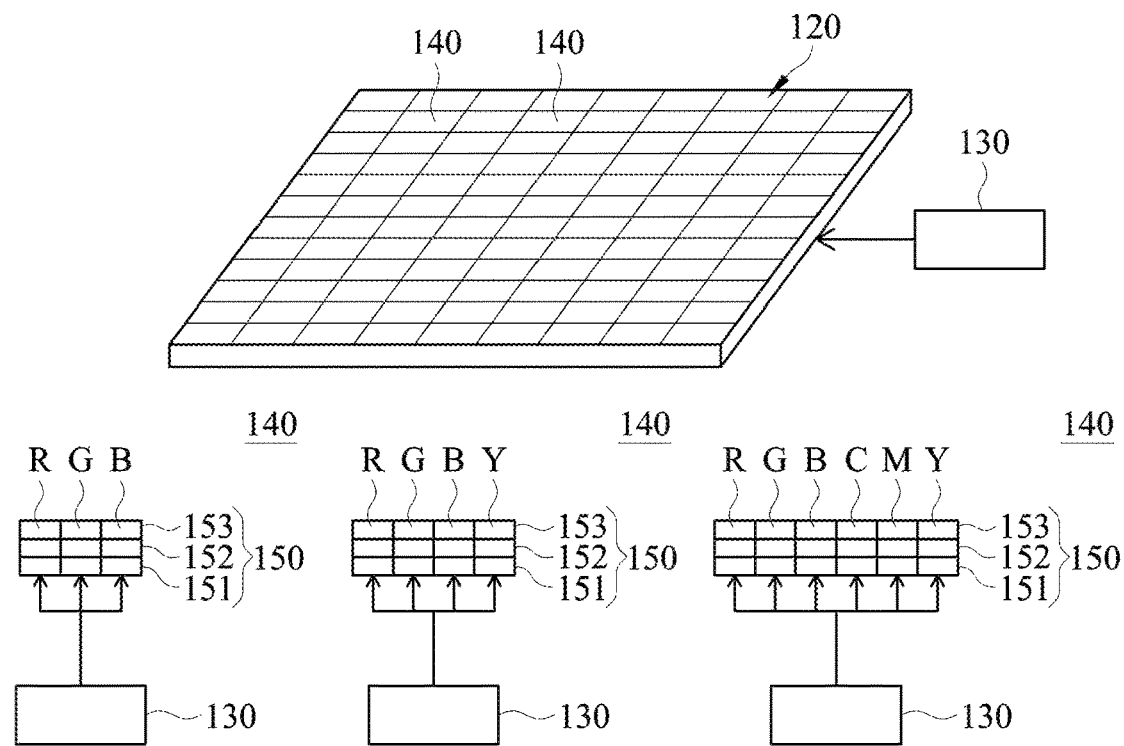
FIG. 7A is a schematic drawing showing basic structure of a first light source of an embodiment according to the present invention.
Figure 7B:
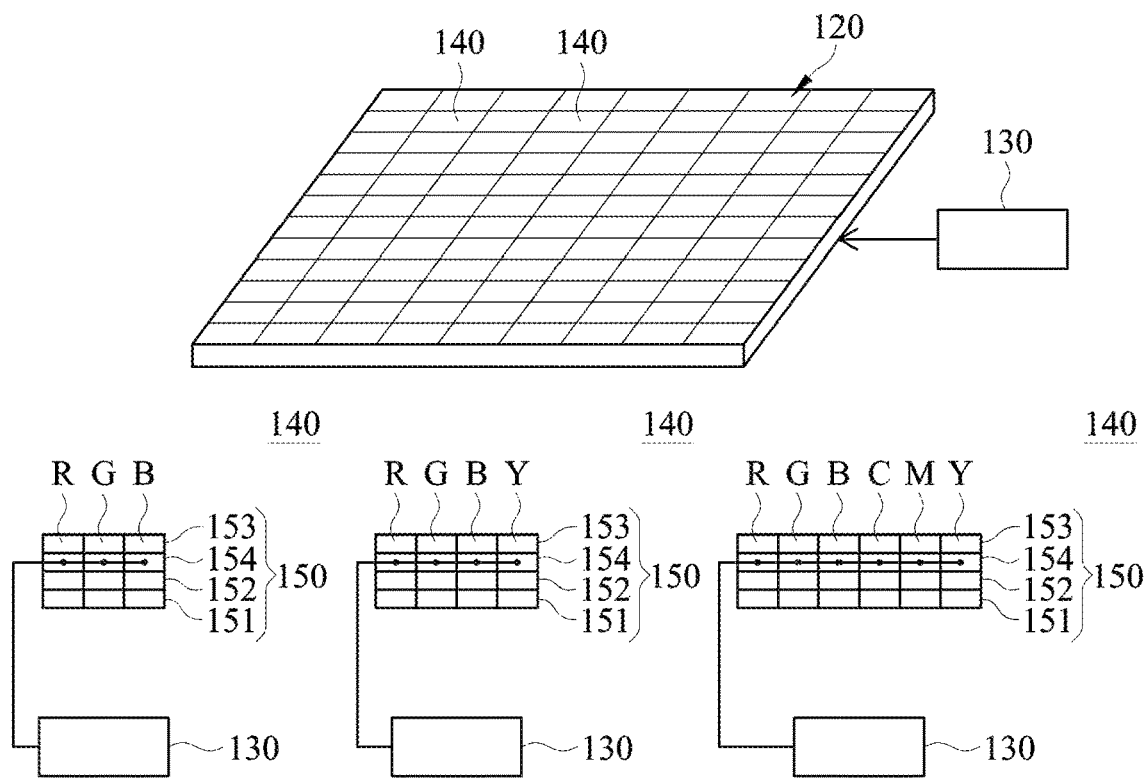
FIG. 7B is a schematic drawing showing basic structure of a first light source provided with liquid crystal control units of an embodiment according to the present invention.

As shown in FIG. 7A and FIG. 7B, the control module 130 mainly controls the optoelectronic image capturing and forming system 110 to capture monochrome images in different colors in turn at different times. That means only one monochrome image in one of the colors is captured by the control module 130 at a time. For example, a red (R) monochrome image, a green (G) monochrome image, and a blue (B) monochrome image of the denture are captured one after another in turn at different times. Or a red (R) monochrome image, a green (G) monochrome image, a blue (B) monochrome image and a yellow (Y) monochrome image of the denture are captured in sequence at different times. Or a red (R) monochrome image, a green (G) monochrome image, a blue (B) monochrome image, a cyan (C) monochrome image, a magenta (M) monochrome image, and a yellow (Y) monochrome image of the denture are taken in turn at different times.

The first light source 120 includes a plurality of pixels 140 each of which consists of a plurality of sub-pixels 150. Each of the sub-pixels 150 is composed of a solid state light source 151, wavelength converting materials (such as phosphors, quantum dots, etc.) 152 and a color filter 153 in one of the three colors, the four colors or the six colors mentioned above. Thereby the first light source 120 can emit light with spectrum having peaks in the regions of the three colors, the four colors or the six colors.

In order to capture monochrome images in turn at different times efficiently, the solid state light sources 151 of the first light sources 120 corresponding to the color filters 153 in different colors are turned on in order at different times under control of the control module 130. At each time point, only the solid state light sources 151 corresponding to the color filter 153 in specific color are tuned on. Thereby the optoelectronic image capturing and forming system 110 can capture a plurality of monochrome images in different colors in turn at different times.

As shown in FIG. 7B, a liquid crystal control unit 154 is provided and disposed between the respective color filters 153 with specific color and the corresponding solid state light sources 151. All the solid state light sources 151 are always on yet the control module 130 controls on/off of the liquid crystal control units 154 for the respective colors in time sequence. Thereby the optoelectronic image capturing and forming system 110 can capture a plurality of monochrome images in separate colors in turn at different times.

As to the display screen 20, it is used to show the teeth images captured by the image scanner 10. Before making the denture, the patient discusses and communicates with the dentist to decide the color, shade, etc. of the denture and make any required adjustments by the images displayed.

In order to avoid color differences between the images shown on the display screen 20 and the images captured by the image scanner 10, the light emitted from the display screen 20 plays an important role. Thus the display screen 20 is designed to have a second emission spectrum 42 while displaying the images.

The second emission spectrum 42 is also a white light composed of a plurality of wavebands with different peak wavelengths and having the same characteristics as the first emission spectrum 41. By using the standard spectrum, the color differences between the display screen 20 and the image scanner 10 are eliminated.

In order to fabricate dentures, the dental technicians need to use images of the teeth in the oral cavity of the patient as the template. However, the dental laboratory where the dental technicians make the dentures and the dental clinic are not at the same place.

The images captured by the image scanner 10 in the dental clinic are displayed on the display screen 20 in the dental laboratory 300 and used as the template for denture fabrication by the dental technicians because they are unable to see or get face-to-face contact with the patients. The display screen 20 in the dental laboratory 300 and the display screen 20 in the dental clinic should be the same, both having the second emission spectrum 42.

The dental technician imitates the teeth image shown on the display screen 20 to create the denture model on a workbench for making the denture. Once there are color differences between the display screen 20 and the lighting device 30 for the workbench, the dental technician can't get the best match of the color and the shade. Thus the color of the denture is unable to match the patient's teeth.

The workbench for making dentures is provided with the lighting device 30 which is designed to have the third emission spectrum 43. The third emission spectrum 43 is also a white light composed of a plurality of wavebands with different peak wavelengths and having the same characteristics as the second emission 42. Thereby the color difference problem between the display screen 20 and the lighting device 30 can be solved by using the standard spectrum.

The above description is only the preferred embodiments of the present invention, and is not intended to limit the present invention in any form. Although the invention has been disclosed as above in the preferred embodiments, they are not intended to limit the invention. A person skilled in the relevant art will recognize that equivalent embodiment modified and varied as equivalent changes disclosed above can be used without parting from the scope of the technical solution of the present invention. All the simple modification, equivalent changes and modifications of the above embodiments according to the material contents of the invention shall be within the scope of the technical solution of the present invention.

What is claimed is:

1. An image scanning, displaying and lighting system for eliminating color differences comprising:
   an image scanner which includes
   an optoelectronic image capturing and forming system,
   a plurality of first light sources which are disposed around the optoelectronic image capturing and forming system and having a first emission spectrum which is a white light composed of a plurality of wavebands with different peak wavelengths in wavelength regions of a plurality of colors, and
   a control module which controls the optoelectronic image capturing and forming system to take monochrome images in each of the colors in time sequence;
   a display screen having a second emission spectrum with the same characteristics as the first emission spectrum; and
   a lighting device having a third emission spectrum with the same characteristics as the second emission spectrum;
   wherein the peak wavelengths of the wavebands of the first emission spectrum, the second emission spectrum, and the third emission spectrum are in the wavelength regions of three colors; each of the first emission spectrum, the second emission spectrum and the third emission spectrum is a three-color spectrum composed of the same red (R), green (G), and blue (B) colors;
   wherein the first light source includes a plurality of pixels each of which consists of a plurality of sub-pixels; each of the sub-pixels is composed of a solid state light source, wavelength converting materials having phosphors or quantum dots, and a color filter in one of the three colors; thereby the first light source is able to emit the three-color spectrum;
   wherein a liquid crystal control unit is disposed between the filters in each of the colors and the corresponding solid state light sources, the control module controls the liquid crystal control units on/off according to each of the colors in time sequence, so that the optoelectronic image capturing and forming system is able to capture a plurality of monochrome images in each of the colors in time sequence.

2. The system as claimed in claim 1, wherein the image scanner is a handheld device.

3. The system as claimed in claim 1, wherein the optoelectronic image capturing and forming system includes an imaging optical system.

4. The system as claimed in claim 1, wherein the optoelectronic image capturing and forming system includes a complementary metal oxide semiconductor (CMOS) component or a charge-coupled device (CCD) used as photoelectric conversion device.

5. The system as claimed in claim 1, wherein the first light source is selected from the group consisting of a ring light source, a planar light source and a curved surface light source.

6. The system as claimed in claim 1, wherein the first light source is a masked light source which includes
   a mask which is an opaque circular wall composed of a reflecting surface therein and a mask opening formed on a skirt portion thereof, and
   a plastic part which is formed on top of the mask, extending toward the inner space of the mask and provided with a connection through-hole while the first light sources are arranged at an outer surface of the plastic part to project the first emission spectrum onto the reflecting surface;
   wherein the connection through-hole is for allowing the optoelectronic image capturing and forming system to insert therein and capture images under light with the first emission spectrum.

7. The system as claimed in claim 1, wherein the solid state light sources of the first light sources corresponding to the color filters in each of the colors are turned on in time sequence under control of the control module so that the optoelectronic image capturing and forming system can capture a plurality of monochrome images in each of the colors in time sequence.

8. An image scanning, displaying and lighting system for eliminating color differences comprising:
   an image scanner which includes
   an optoelectronic image capturing and forming system,
   a plurality of first light sources which are disposed around the optoelectronic image capturing and forming system and having a first emission spectrum which is a white light composed of a plurality of wavebands with different peak wavelengths in wavelength regions of a plurality of colors, and
   a control module which controls the optoelectronic image capturing and forming system to take monochrome images in each of the colors in time sequence;
   a display screen having a second emission spectrum with the same characteristics as the first emission spectrum; and
   a lighting device having a third emission spectrum with the same characteristics as the second emission spectrum;
   wherein the peak wavelengths of the wavebands of the first emission spectrum, the second emission spectrum and the third emission spectrum are in the wavelength regions of four colors; each of the first emission spectrum, the second emission spectrum, and the third emission spectrum is a four-color spectrum composed of the same red (R), green (G), blue (B), and yellow (Y) colors;
   wherein the first light source includes a plurality of pixels each of which consists of a plurality of sub-pixels; each of the sub-pixels is composed of a solid state light source, wavelength converting materials having phosphors or quantum dots, and a color filter in one of the four colors; thereby the first light source is able to emit the four-color spectrum;
   wherein a liquid crystal control unit is disposed between the filters in each of the colors and the corresponding solid state light sources, the control module controls the liquid crystal control units on/off according to each of the colors in time sequence, so that the optoelectronic image capturing and forming system is able to capture a plurality of monochrome images in each of the colors in time sequence.

9. The system as claimed in claim 8, wherein the solid state light sources of the first light sources corresponding to the color filters in each of the colors are turned on in time sequence under control of the control module so that the optoelectronic image capturing and forming system can capture a plurality of monochrome images in each of the colors in time sequence.

10. An image scanning, displaying and lighting system for eliminating color differences comprising:

an image scanner which includes
an optoelectronic image capturing and forming system,
a plurality of first light sources which are disposed around the optoelectronic image capturing and forming system and having a first emission spectrum which is a white light composed of a plurality of wavebands with different peak wavelengths in wavelength regions of a plurality of colors, and
a control module which controls the optoelectronic image capturing and forming system to take monochrome images in each of the colors in time sequence;
a display screen having a second emission spectrum with the same characteristics as the first emission spectrum; and
a lighting device having a third emission spectrum with the same characteristics as the second emission spectrum;
wherein the peak wavelengths of the wavebands of the first emission spectrum, the second emission spectrum and the third emission spectrum are in the wavelength regions of six colors; each of the first emission spectrum, the second emission spectrum, and the third emission spectrum is a six-color spectrum composed of the same red (R), green (G), blue (B), cyan (C), magenta (M) and yellow (Y) colors;
wherein the first light source includes a plurality of pixels each of which consists of a plurality of sub-pixels; each of the sub-pixels is composed of a solid state light source, wavelength converting materials having phosphors or quantum dots, and a color filter in one of the six colors; thereby the first light source is able to emit the six-color spectrum;
wherein a liquid crystal control unit is disposed between the filters in each of the colors and the corresponding solid state light sources, the control module controls the liquid crystal control units on/off according to each of the colors in time sequence, so that the optoelectronic image capturing and forming system is able to capture a plurality of monochrome images in each of the colors in time sequence.

11. The system as claimed in claim 10, wherein the solid state light sources of the first light sources corresponding to the color filters in each of the colors are turned on in time sequence under control of the control module so that the optoelectronic image capturing and forming system can capture a plurality of monochrome images in each of the colors in time sequence.

* * * * *